United States Patent
Mayer et al.

(10) Patent No.: US 9,017,380 B2
(45) Date of Patent: Apr. 28, 2015

(54) SURGICAL METHOD, KIT OF PARTS, AND IMPLANT

(75) Inventors: Jörg Mayer, Niederlenz (CH); Urs Weber, Evilard (CH); Andrea Müller, Neftenbach (CH); Thomas Knecht, Hausen (CH); Philipp Seiler, Niederdorf (CH); Christopher Rast, Biel (CH); Marcel Aeschlimann, Ligerz (CH); Laurent Torriani, Lamboing (CH)

(73) Assignee: Woodwelding AG, Stansstad (CH)

( * ) Notice: Subject to any disclaimer, the term of this patent is extended or adjusted under 35 U.S.C. 154(b) by 934 days.

(21) Appl. No.: 11/694,249

(22) Filed: Mar. 30, 2007

(65) Prior Publication Data

US 2007/0265704 A1 Nov. 15, 2007

Related U.S. Application Data

(60) Provisional application No. 60/744,167, filed on Apr. 3, 2006.

(51) Int. Cl.
*A61B 17/56* (2006.01)
*A61B 17/58* (2006.01)
(Continued)

(52) U.S. Cl.
CPC ......... *A61B 17/0469* (2013.01); *A61B 17/0642* (2013.01); *A61B 17/68* (2013.01); *A61B 17/8085* (2013.01); *A61B 17/8605* (2013.01); *A61B 2017/06057* (2013.01); *A61F 2/0063* (2013.01);
(Continued)

(58) Field of Classification Search
USPC .................. 623/17.12; 606/75, 285, 151, 232
See application file for complete search history.

(56) References Cited

U.S. PATENT DOCUMENTS

| 3,367,809 A | * | 2/1968 | Soloff | 156/73.1 |
| 5,607,427 A | * | 3/1997 | Tschakaloff | 606/284 |

(Continued)

FOREIGN PATENT DOCUMENTS

| WO | WO 02069817 A1 * | 9/2002 | A61B 17/68 |
| WO | 2008/116203 A2 | 9/2008 | |

OTHER PUBLICATIONS

Aeschlimann et al; U.S. Appl. No. 10/415,454 for "Implants, Device and Method for Joining Tissue Parts", filed Aug. 27, 2003.
(Continued)

*Primary Examiner* — David Bates
(74) *Attorney, Agent, or Firm* — Rankin, Hill & Clark LLP (57) ABSTRACT

A surgical method is provided, the method including the steps of: providing an artificial or allograft flexible planar structure; providing an implant, the implant including material liquefiable by mechanical oscillation, exposing a surface region of hard tissue or hard tissue substitute material; positioning the implant on an exposed area of the hard tissue or hard tissue substitute material; and fastening the implant to the hard tissue or hard tissue substitute material by impinging the proximal end of the implant with mechanical oscillation and simultaneously pressing the implant against the hard tissue or hard tissue substitute material while the distal end of the implant protrudes into a cavity of the hard tissue or hard tissue substitute material and regions of the liquefiable material are in contact with the hard tissue or hard tissue substitute material, and thereby liquefying at least a portion of the liquefiable material, and letting the liquefiable material resolidify.

17 Claims, 7 Drawing Sheets

(51) Int. Cl.
*A61B 17/064* (2006.01)
*A61B 17/84* (2006.01)
*A61F 2/00* (2006.01)
*A61B 17/08* (2006.01)
*A61B 17/04* (2006.01)
*A61B 17/80* (2006.01)
*A61B 17/68* (2006.01)
*A61B 17/86* (2006.01)
*A61F 2/08* (2006.01)
*A61B 17/06* (2006.01)
*A61F 2/30* (2006.01)
*A61F 2/46* (2006.01)

(52) U.S. Cl.
CPC ....... *A61F 2/0811* (2013.01); *A61F 2002/0835* (2013.01); *A61F 2002/0858* (2013.01); *A61F 2002/0888* (2013.01); *A61F 2002/30065* (2013.01); *A61F 2002/30579* (2013.01); *A61F 2002/4683* (2013.01); *A61F 2210/0071* (2013.01)

(56) References Cited

U.S. PATENT DOCUMENTS

| | | | |
|---|---|---|---|
| 6,080,161 | A | 6/2000 | Eaves, III et al. |
| 6,447,516 | B1 | 9/2002 | Bonutti |
| 6,592,609 | B1 | 7/2003 | Bonutti |
| 6,635,073 | B2 | 10/2003 | Bonutti |
| 6,921,264 | B2 | 7/2005 | Mayer et al. |
| 6,955,540 | B2 | 10/2005 | Mayer et al. |
| 7,008,226 | B2 | 3/2006 | Mayer et al. |
| 7,087,073 | B2 | 8/2006 | Bonutti |
| 7,250,055 | B1 * | 7/2007 | Vanderwalle .................. 606/92 |
| 7,335,205 | B2 * | 2/2008 | Aeschlimann et al. ....... 606/232 |
| 2004/0030341 | A1 * | 2/2004 | Aeschlimann et al. ......... 606/72 |
| 2004/0030342 | A1 * | 2/2004 | Trieu et al. ...................... 606/72 |
| 2006/0089646 | A1 * | 4/2006 | Bonutti ......................... 606/61 |
| 2007/0270833 | A1 | 11/2007 | Bonutti et al. |
| 2008/0021474 | A1 | 1/2008 | Bonutti et al. |
| 2008/0039845 | A1 | 2/2008 | Bonutti et al. |
| 2009/0024161 | A1 | 1/2009 | Bonutti et al. |
| 2010/0211120 | A1 | 8/2010 | Bonutti et al. |

OTHER PUBLICATIONS

Mayer et al.; U.S. Appl. No. 10/530,684 for "Implant That Can Be Implanted in Osseous Tissue, Method for Producing Said Implant and Corresponding Implant", filed Apr. 25, 2005.

Mayer et al.; U.S. Appl. No. 10/528,867 for "Method for Promotion of Tissue Regeneration on Wound Surfaces and Device and Treatment Instrument or Implant for Carrying Out Said Method", filed Apr. 25, 2005.

Mayer et al.; U.S. Appl. No. 11/568,553 for "Light Diffuser and Process for Producing the Same", filed Nov. 1, 2006.

\* cited by examiner

SURGICAL METHOD, KIT OF PARTS, AND IMPLANT

BACKGROUND OF THE INVENTION

1. Field of the Invention

The invention lies in the field of medical technology and relates to a method of fixing an object within the human or animal body by means of a flexible planar structure, for example a web. It further relates to a kit of parts for carrying out said method and to an implant.

2. Description of Related Art

It has been known to use artificial membranes in surgery for covering soft tissue, for example in the case of a hernia, such as an inguinal hernia. Examples of such membranes are fabrics. For many applications it would be desirable, however, to extend the possibilities of existing surgical methods and of devices used therefor.

SUMMARY OF THE INVENTION

It is an object of the invention to provide a surgical method which introduces new possibilities of fixing tissue parts or artificial objects within a human or animal body, of correcting the position of tissue parts or artificial objects, or of applying forces to tissue parts or artificial objects.

According to an aspect of the invention, a surgical method is provided, the method comprising the steps of:

Providing an artificial or allograft or autograft flexible planar structure;

Providing an implant, said implant comprising a proximal end and a distal end and further comprising a surface region of material liquefiable by mechanical movement, or further comprising a hollow space that is at least partially filled by material liquefiable by mechanical movement and at least one channel (preferably a plurality of channels) between the hollow space and an implant surface, so that the liquefiable material may reach a surface region when a mechanical movement is applied to the liquefiable material;

Exposing a surface region of hard tissue or hard tissue substitute material;

Positioning the implant on an exposed area of the hard tissue or hard tissue substitute material; and Fastening the implant to the hard tissue or hard tissue substitute material by:

Impinging the proximal end of the implant with mechanical movement and simultaneously pressing the implant against the hard tissue or hard tissue substitute material while the distal end of the implant protrudes into a cavity of the hard tissue or hard tissue substitute material and regions of the liquefiable material are in contact with the hard tissue or hard tissue substitute material, and thereby liquefying at least a portion of the liquefiable material; and letting the liquefiable material resolidify;

wherein the flexible planar structure is fastened to the implant, either before impinging the implant by mechanical movement or while impinging the implant by mechanical movement or after impinging the implant by mechanical movement.

Flexible in the context of this text means "offering essentially no resistance against bending", i.e. having no flexural rigidity or only having a small flexural rigidity. Especially, the flexible planar structure is not resilient in the sense of being capable of excerpting a spring force.

The hard tissue or hard tissue substitute material may be a bone tissue, such as a live bone tissue. Indeed, the advantages of the approach according to the invention are most evident for applications in respect to live bone tissue, since for such applications it is often important that the implantation is quick and provides a high primary stability. The hard tissue or hard tissue substitute material, however, as an alternative, may not be live bone tissue or bone substitute material (such as bone cement) or another hard tissue, such as dentin or possibly cartilage, or their substitute material. In the following discussion, the hard tissue or hard tissue substitute material is primarily mentioned as bone tissue; however, the teaching also applies to the other kinds of hard tissue or hard tissue substitute material.

The method may be carried out in situ with live bone tissue. As an alternative, it may also be carried out ex situ.

The mechanical movement is preferably a mechanical oscillation, especially ultrasonic vibration. It may, in certain special cases, also be an unidirectional movement such as a rotational movement.

The invention thus proposes to fasten a web (or other flexible planar structure) to a bone tissue (or other hard tissue or to hard tissue substitute material) in order to influence the position of tissue parts or artificial implants and/or to apply forces thereto. Especially, the invention proposes to do so by means of a method providing a connection that is permanent and tight but nevertheless allows for some remaining resilience. For example, the web may be fastened by means of a plurality of comparably small implants so as to distribute potential forces upon the web on a large area.

The flexible planar structure can be any kind of web (in the broadest sense of the word), for example any membrane or foil or fabric. Examples of such webs include artificial fabrics such as webs of plastic material, of metal fibers, of other fibers, and hybrid artificial fabrics. Such webs may be non-wovings, weavings, knittings, breadings, embroidered textiles or other fabrics. The advantages and disadvantages of different textile structures for medical applications are, for example, discussed in the publicly available PhD Thesis for the Swiss Federeal Institute of Technology Zurich by Ziya Erdal Karamuk "Embroidered Textiles for Medical Applications: New Design Criteria with Respect to Structural Biocompatibility".

Further examples of webs include foils or membranes, such as polymer films or also porous films e.g. made of materials e.g. expanded tetrafluorpolyethylene (ePTFE), commercially available as membranes from Gore & Associates.

As yet another alternative, the flexible planar structure can also be a natural tissue structure such as an allograft tendon or ligament, an allograft dura, chondral tissue or decalcified primarily collagenous sheet like material.

Whereas the flexible planar structure can have any shape, usually the extension in one dimension (thickness) is clearly smaller than the extension in the other dimensions (length, width). For example, the thickness may be smaller than the smaller of the length and the width by at least a factor of 5, preferably at least a factor of 10, usually by at least a factor of 20 or more. The flexible planar structure may have a lengthy shape (ratio between length and width greater than 10), but the invention is also especially suited for flexible planar structures where the ratio of the length and the width is smaller than 10.

There are two alternative ways of producing the bone tissue cavity. As a first option, the cavity of the bone tissue may be pre-fabricated by making (for example by drilling) a bore in the bone tissue, wherein the width and depth of the hole are at most as large as the width and length of the portion of the implant that will finally protrude into the cavity. The implant may then be of any suitable material composition, provided its surface has the necessary portions of liquefiable material or may be provided, from the inside through channels (openings) with such liquefiable material. It may for example be a hybrid with a core of a first plastic material, of a metal or of a ceramic or reinforced plastic and a cladding of thermoplastic material. Alternatively, the implant may also be completely made of the thermoplastic material. As yet another alternative, the implant may comprise a hard shell, not of thermoplastic material, with a filling of thermoplastic or thixotrope material and openings in the shell through which the thermoplastic or thixotrope material exits during implantation.

As a second option, the cavity may be produced by the introduction of the implant into the bone tissue by means of mechanical oscillations (preferably ultrasonic vibrations). Before this, the Periosteum may be removed at the appropriate location. The implant then preferably comprises a hard core of a metal, e.g. of titanium, of a titanium alloy, or of another suitable metallic or ceramic material such as zirconia, a possibly reinforced plastic material, another material or a combination of at least two of these. The implant may also comprise a cutting edge for cutting into the bone tissue and/or a pronounced tip to be driven into the bone tissue. The cutting edges cutting into the bone tissue during implantation may also contribute to the anchoring of the implant. Means especially adapted for driving the implant into bone tissue, such as self-reaming structures, are for example described in WO 2005/079 696.

Further teachings and alternative versions of implants may, for example, be found in WO 02/069 817, WO 2004/017 857, or WO 2005/079 696, the teachings of all of which are incorporated herein by reference.

The liquefiable material preferably is provided at a surface portion of the implant. In this case, the liquefiable material is preferably thermoplastic.

As an alternative, the liquefiable material may be arranged in a hollow space of the implant. Then, it forms the surface region of liquefiable material on the implant that can be brought into contact with the bone tissue and can be excited by mechanical oscillation only after it has been excited and/or pressed out through channels (openings) onto the surface. In the case of the liquefiable material being positioned in a hollow space of the implant, the mechanical vibration is advantageously not applied to the implant until the implant is positioned in the cavity and then only to the liquefiable material. In this case, the liquefiable material may be a thermoplastic material or a thixotropic, particulate, hydraulic or polymeric cement, as also used in orthopaedics for anchoring implants or e.g. for the infiltration of diseased collapsed vertebrae.

Simultaneously, with the insertion of the implant into the bone tissue cavity or with producing the cavity by introducing the implant, respectively, the implant is impinged with mechanical vibration. This causes the liquefiable material, advantageously a thermoplastic material, to liquefy at points of contact with the bone tissue. Since the bone tissue along the cavity wall comprises unevenness and/or pores and/or artificially made retention structures, for example threads or undercuts, the material liquefied by the oscillations penetrates these structures and is thus brought into intensive contact with the bone tissue surface. This is especially the case in the spongy bone tissue but also in the cortical bone tissue. The cavity wall may in addition comprise structures specifically fashioned for this purpose. Having set (solidified) again, the liquefiable material forms a link between the implant and the bone tissue interlocking the two by positive fit and possibly adhesive bond. The penetration of these structures by the liquefiable material thus results in an anchoring of the implant in the bone tissue by a kind of micro-interlocking. This effect and methods for implanting, by mechanical oscillations implants in bone tissue and implants therefor are described in mentioned WO 02/069 817, WO 2004/017 857, and WO 2005/079 696, all incorporated herein by reference.

The implant according to the invention is thus stabilized in the cavity immediately after the implantation by its connection with the bone tissue through the liquefiable material, wherein this stabilization is effective against pressure and tension (e.g. parallel to an implant axis) as well as, as the case may be, against torsional loading.

All named effects lend the implant, according to the invention, a primary stability, which is in most cases sufficient to withstand loading immediately after implantation. The connective structures of thermoplastic material possess a comparable or lesser elastic modulus than the local recipient bone structure, e.g. the osseous trabeculus), and their ability to creep make them particularly advantageous for absorbing shocks and for reducing excessive stress. Due to body movements, flexible structures tend to be subject to recurring forces. As a consequence, on the one hand, state-of-the-art non-flexible connections would bring about the danger that they start loosening after some time. Thus, adhesion to live tissue, by natural tissue growth, of an object to be fixed is prevented. If a connection is made too tight, on the other hand, natural tissue growth has been proven to be slow and flawed. The method according to the invention, however, features the substantial advantage of providing a non-detachable connection by which the bone tissue and the implant are at a relative rest against each other. Nevertheless, the liquefiable material's elasticity prevents shielding the bone-implant interface from those moderate stresses that are known to stimulate osseointegration. Typical values for such stress induced stimulative strains are between 0.05% to 0.5%. As a consequence, osseointegration by natural tissue growth of the implant to the bone tissue and/or of the flexible planar structure to the bone tissue is enhanced. At the same time, these connections prevent major displacements between implant and bone tissue and thus between the bone tissue and the flexible planar structure, which displacements would lead to the disruption of the osseointegration process.

Detachable connections may—and will—detach when subject to recurring forces for a long time. The method according to the invention, in contrast, allows the rigid structure of the body, namely the bones, to be used for fixing or adjusting the position of a thin flexible structure in a force bearing manner and by a non-detachable, permanent connection.

Forces tearing the flexible planar structure may be especially well absorbed if the connection is a large area connection. This may be done by using a plurality of implants all implanted by the process in accordance with the above description. Different implants may, according to a special embodiment, be connected to each other by bridge like structures.

The connection between the implant(s) and the flexible planar structure may be brought about in different ways:
A. Pre-fabricated connection: The implant(s) and the flexible planar structure may be a one-piece element, i.e. they are manufactured from one piece of material or are fastened to each other before operation (ex situ).
B. Connection by macroscopic positive fit: The implants may, for example, protrude through openings in the flexible planar structure and may have a head-like bulge or a claw like structure preventing the flexible planar structure from loosening. The openings may be pre-fabricated, produced ex situ or in situ with an appropriate tool or may be brought about by piercing by a tip of the implant itself.

C. In accordance with a variant of option B, a bulge-like structure may be manufactured only after both the implant(s) and the flexible planar structure have been placed. The implant then functions as a kind of rivet. Especially preferred are embodiments where the implant comprises a tip-like structure towering towards the proximal side. The flexible planar structure may then, after the implant(s) have been set, be pre-tensioned and be lowered onto the bone with the protruding implants' tips. Thereafter the tips are deformed into the bulges. This may be done by ultrasonic vibration, heating, mechanical deformation or a combination of these. This embodiment is especially suited for placing the flexible planar structure under tension.

D. In accordance with a variant of option B, a plurality of implants may be connected by a bridge like element that prevents the flexible planar structure from loosening.

E. Connection by micro-interlocking: The flexible planar structure may be porous and/or absorbent and/or comprise unevennesses, and the implant may comprise liquefiable material in the region where it is in contact with the flexible planar structure. Then, like for the bone tissue, the liquefiable material may penetrate these structures resulting in an anchoring of the implant in the flexible planar structure and thus in an intimate connection between the implant and the flexible planar structure.

F. Connection by welding: If the flexible planar structure is liquefiable and the implant comprises liquefiable portions in a region in contact with the flexible planar structure, such material portions may fuse together to form an intimate connection.

"Porous" in this context includes a textile, for example meshed, structure where the spacings between the filaments act as open pores.

The different options may be combined with each other. Especially, it is preferred to combine either of options B, C, and D with option E and/or option F. A combination of option E and option F is achieved if the fabric includes (or even consists of) fibers that are thermoplastic and may be liquefied under the conditions during implantation and/or fastening the flexible planar structure to the implant.

In the case of option E. (micro-interlocking of the flexible planar structure with the implant(s)) and/or option F., the melting of the liquefiable material of the implant may be done in the same step with the implantation. Then, the liquefiable material penetrating the bone tissue structures and the liquefiable material penetrating the flexible planar structure are melted in one step by applying ultrasonic vibrations to the implant by one tool. As an alternative, this may be a two-step process, where for example first the liquefiable material in contact with the bone tissue is liquefied by applying oscillations with a first amplitude and frequency and then the liquefiable material in contact with the flexible planar structure is liquefied by applying oscillations with a second amplitude and frequency and/or applied at second surface portions not identical surface portions to which the first oscillations are applied. Instead of or in addition to being melted by ultrasonic vibration, the proximal head of the implant may also be deformed by heat. Also, a combination with deformation by mechanical deformation.

The implant according to the invention may, according to a preferred embodiment, be inserted into the bone tissue cavity without substantial rotation (in particular without rotation greater than 360°). It may be inserted substantially in the direction of an implant axis.

One of the achievements of the invention is that it makes a quick anchoring of the flexible planar structure in the hard tissue possible. This is since the procedure of fastening the implant to the hard tissue by having structures of the hard tissue be interpenetrated—as disclosed above—by liquefied material that re-solidifies is quick and provides a high primary stability. Also, the step of fastening the flexible planar structure and the implant to each other may be a quick step that may include melting thermoplastic material in a zone of contact between the implant and the flexible planar structure. Said thermoplastic material may stem from the implant, from the flexible planar structure or from both, and may cause a welding connection and/or may interpenetrate pores, for example, of the flexible planar structure being a fabric. Finally, optionally the steps of fastening the implant to the hard tissue or tissue substitute material and of fastening the flexible planar structure to the implant may be combined in one single step and, for example, be done with a single tool.

The implant according to the invention may comprise a cylindrical portion or a portion tapered towards its distal end. It may further comprise energy concentrators, edges, and/or protrusions.

The liquefiable material to be applied in the implant according to the invention may, depending on the application, be biologically resorbable. As an alternative, the material may be biologically compatible, i.e. of bone-friendly and advantageously osseointegrative character. Also surface regions of the implant which are not liquefiable, but come into contact with bone tissue may be biologically compatible. On these surface areas osseointegration of the implant can begin immediately after implantation and can successively relieve the anchoring by the resorbable thermoplastic material. It is possible also to use a non-resorbable thermoplastic material in such a manner that its anchoring in the bone tissue permanently complements or even replaces the anchoring by osseointegration.

Biologically resorbable liquefiable materials suitable for the individual implant according to the invention are: thermoplastic polymers based on lactic and/or gluconic acid (PLA, PLLA, PGA, PLGA etc) or polyhydroxy alkanoates (PHA), polycaprolactones (PCL), polysaccharides, polydioxanones (PD), polyanhydrides, polypeptides, trimethyl-carbonates (TMC), or corresponding copolymers, or mixed polymers, or composites containing said polymers. Suitable non-resorbable thermoplastic materials are e.g. polyolefines (e.g. polyethylene), polyacrylates, polymethacrylates, polycarbonates, polyamides, polyesters, polyurethanes, polysulfones, liquid-crystal-polymers (LCPs), polyacetals, halogenated polymers, in particular halogenated polyolefines, polyphenylene sulphones, polysulfones, polyethers, or corresponding copolymers and mixed polymers or composites containing said polymers. Composites included composites generated by adding fillers (particulates, fibers, whiskers, . . . ) from materials like calcium phosphates, phosphate based glasses (bioglasses), carbonates, sulfates, high atom number comprising elements for x-ray contrast. The materials may be provided with pharmacologically active substances, e.g., antibiotic agents, stimulating agents (growth factors), antiinflammatory agents, zytostatic agents, combinations of these, and/or precursors thereof.

Particularly suitable as resorbable liquefiable materials are: poly-LDL-lactide (e.g. available from Bbhringer under the trade name Resomer LR708) or poly-DL-lactide (e.g.

available from Böhringer under the trade name Resomer R208); as non-resorbable liquefiable material: polyamide 11 or polyamide 12.

The flexible planar structure may serve for one or more of the following purposes:

It may be an artificial or allograft ligament or tendon.

It may be an artificial or allograft based dural tissue like material to repair soft tissue laesion e.g. of the dura or of the spinal cord.

It may serve as an none-adhesion layer to prevent tissue adhesions after surgical intervention e.g. to cover the vertebral access side after insertion of a interbody fusion device or intervertebral disc.

It may serve as an adhesion promotion membrane allowing or stimulating tissue ingrowth.

It may serve for stabilizing or repairing skeletal structures such as the vertebra or sub-structures thereof, e.g., the annulus fibrosus.

The flexible planar structure may be part of an implant, e.g. an extensional membrane to attach bone fragments or used to attach the implant to a distinct osseous bonding site, such as a nucleus prosthesis formed as a textile bag filled with a gel, which is introduced into the intervertebral disk cavity after nucleotomy and which swells therein.

The flexible planar structure may also be a part of a larger implant (distinct from the implants used to affix the flexible planar structure to the bone material), for example a shoulder prosthesis.

If the flexible planar structure is transparent, it may be used to couple light into the (also transparent) implant, or the implant may be used to couple light into the flexible planar structure which, for example, covers a tumor, wherein the light is used to stimulate a tumor antagonizing agent.

The flexible planar structure may be positioned and fixed so as to form a bag-like container holding some element or material, for example medication to be slowly resorbed, through the flexible planar structure, by the body.

The flexible planar structure may also be impregnated with an agent.

The flexible planar structure may serve as a spacer between elements of a, for example, osteoarthritic joint—according applications to the trapeziometacarpal (TMC) joint are, for example, known from the company SBI.

The flexible planar structure may release pharmacologically active substances e.g. to stimulate a healing process or a growth process by added agents, by its composition and/or by its structure (pore architecture).

The flexible planar structure may be used for positioning and holding in place soft tissue and/or soft tissue substitute material within the body. This includes the prevention and/or repair of a hernia such as a hernia of the intervertebral disc. An embroidered fabric for holding in place of a intervertebral disc implant is, for example, commercially offered by Nuvasive.

The flexible planar structure may be used to cover cavities in bone, e.g. after bone harvesting and to serve as bone guidance membrane.

The flexible planar structure may be used to cover soft tissue cavities and to guide soft tissue regeneration e.g. for cartilage regeneration being a periosteal flap or an allograft or an artificial membrane.

The flexible planar structure could also act as scaffold for tissue ingrowth either in vivo or in-vitro by being pre-seeded and cultivated with suitable cells (e.g. stem cells, chondrocytes, osteoblasts, fibroblasts, cells related to the tendonous endplate) to further enhance the repair and regenerative capacity of the construct.

The flexible planar structure may serve as vascular prosthesis.

The flexible planar structure may be used for embedding at least one conductive coil for achieving, with the aid of the flexible planar structure, local high resolution in an MRI image.

The flexible planar structure may embed nanomagnetic particles or other resistance elements with the aid of which locally, by alternating fields, hyperthermias may be caused and used for antagonizing a tumor.

The flexible planar structure may embed identification elements such as RFID tags.

Two or more of the above can be combined where such combination makes sense.

According to an other aspect of the invention, a surgical method is provided, the method comprising the steps of:

Providing an artificial or allograft flexible planar structure;

Providing a plurality of implants, each comprising a proximal end and a distal end and further comprising a surface region of material liquefiable by mechanical oscillation, or further comprising a hollow space that is at least partially filled by material liquefiable by mechanical oscillation and at least one channel between the hollow space and an implant surface, so that the liquefiable material may reach a surface region when a mechanical oscillation is applied to the liquefiable material;

Exposing a surface region of live bone tissue;

Positioning the implants on an exposed area of the bone tissue and positioning at least a section the flexible planar structure on said exposed area, so that the implants reach through openings in the flexible planar structure;

Impinging the proximal end of the implants with mechanical oscillation and simultaneously pressing the implant against the bone tissue while the distal ends of the implants protrude into cavities of the bone tissue and regions of the liquefiable material are in contact with the bone tissue, and thereby liquefying at least a portion of the liquefiable material;

Liquefying, by mechanical vibration, liquefiable material of the implants being in contact with the flexible planar structure and thereby penetrating at least one of pores and of spaces of the flexible planar structure by the liquefied liquefiable material; and letting the liquefiable material resolidify.

According to yet another aspect, the invention concerns a kit of parts for performing a surgical operation, for example an operation according to any one of the features discussed in this text, the kit comprising:

an artificial or allograft flexible planar structure, and further comprising a plurality of implants, each comprising
  a proximal end and a distal end,
  a surface region of material liquefiable by mechanical movement, or a hollow space that is at least partially filled by material liquefiable by mechanical movement and at least one channel between the hollow space and an implant surface, so that the liquefiable material may reach a surface region when a mechanical movement is applied to the liquefiable material, and
  a fastening means for fastening the implant to the flexible planar structure before being implanted, while being implanted, or after being implanted.

For example, the flexible planar structure may comprise a plurality of pores into which liquefied material from the implant may interpenetrate so that an intimate connection may be formed. To this end, the implant may comprise surface portions that are, when the flexible planar structure and the implant are in their destined position, in contact with the flexible planar structure. The flexible planar structure may, for example, be a fabric, where the pores are spaces between the fibers. In addition or as an alternative, the flexible planar structure may be thermoplastic. The flexible planar structure may, for example, be foil-like.

The fastening means of the implant may comprise the mentioned surface portions of thermoplastic material in contact with the flexible planar structure. In addition, or as an alternative, the fastening means may include a particular shape such as a proximal broadening, which serves for fastening the flexible planar structure, for example like the head of a nail, like a hook, a bridge etc. In addition or as an alternative, the fastening means may be rivet-like, i.e. formed after the positioning of the implants and the flexible planar structure only. Further options are possible and described in the following description.

According to a special embodiment, the flexible planar structure may be a suturing fabric for serving as a base for suturing an element to the hard tissue.

An even further aspect of the invention concerns an implant comprising
- a proximal end and a distal end,
- a surface region of material liquefiable by mechanical movement, or a hollow space that is at least partially filled by material liquefiable by mechanical movement and at least one channel between the hollow space and an implant surface, so that the liquefiable material may reach a surface region when a mechanical movement is applied to the liquefiable material, and
- a fastening means for fastening the implant to the flexible planar structure before being implanted, while being implanted, or after being implanted.

DETAILED DESCRIPTION OF THE INVENTION

Figure 1:
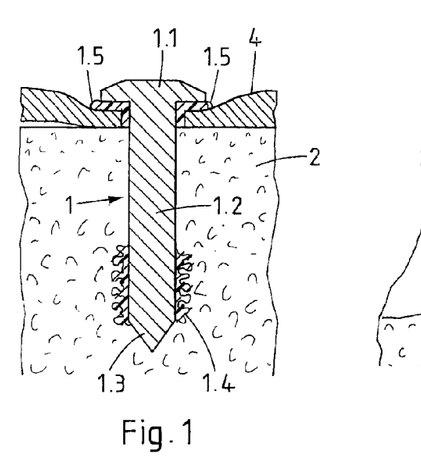
FIG. 1 shows an implant and a flexible, planar structure attached to a bone tissue in cross section.

FIG. 1 shows an implant 1 with a head 1.1 formed at a proximal end, a cylindrical or tapering shaft 1.2, and a tip 1.3 at a distal end. The implant is introduced into a cavity formed in a bone tissue 2. An artificial flexible planar structure, namely a fabric 4 lies on the bone tissue and is fastened thereto by means of the implant 1. The fabric 4 may, for example, be a fabric of a kind as such known in surgery, for example a mesh of knitted nonabsorbable polypropylene filaments, of other plastic material filaments, of metal filaments (such as titanium filaments), or of any other tissue friendly or resorbable material. The fabric comprises an aperture trough which is penetrated by the implant. The aperture may have been produced in that the fabric 4 was pierced by the implant 1. As an alternative, the aperture may have been pre-fabricated ex situ.

The implant is anchored in the bone tissue 2 in that it comprises a surface region 1.4 of thermoplastic material that has been liquefied by mechanical vibration and resolidified after penetrating structures of the adjacent bone tissue, as described above.

Optionally, the surface region that includes the liquefiable material may extend to the place where the implant is in contact with the fabric 4, or the implant may comprise a second surface region including liquefiable material. Such an optional second surface region 1.5 is sketched in FIG. 1. Depending on the porosity of the flexible planar structure, liquefiable material may then also penetrate structures of the flexible planar structure and cause an anchoring of the implant also in the flexible planar structure, strengthening the fixation of the flexible planar structure to the implant.

In this and in all subsequently described embodiments, the implant may, instead of being provided with a surface region of liquefiable material in its initial state, also comprise liquefiable material that gets to the surface, for example, from an inside of the implant.

Figure 2:
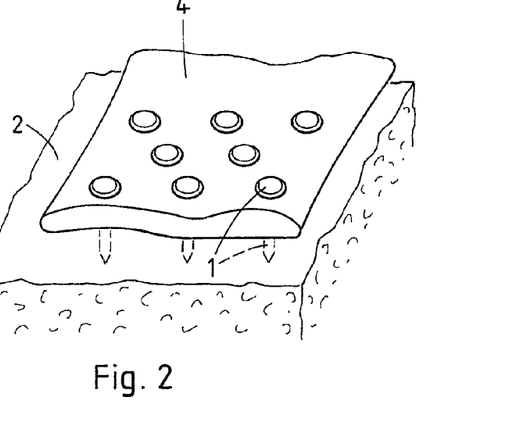
FIG. 2 is a view of a flexible planar structure fastened to a bone tissue by means of a plurality of implants.

For reliably fixing the flexible planar structure within the body, it is advantageous to have a fixation that is effective on a large area. One possibility of achieving this is illustrated in FIG. 2. A plurality of implants 1 is used for fixing a section of a fabric 4 to a bone tissue 2. The implants during implantation directly penetrate the fabric 4. The implants may be of the kind described in FIG. 1. The embodiment shown in FIG. 2 features the following advantages:

- The strength of the anchoring in the bone tissue and of the attachment of the flexible planar structure to the bone tissue is high;
- The anchorage is relatively easy to be made;
- The tension of the fabric 4 can be controlled;
- The implantation brings about a low trauma only, especially if the implants are chosen to be comparably small;
- The position of the fabric can be chosen freely.

Figure 3:
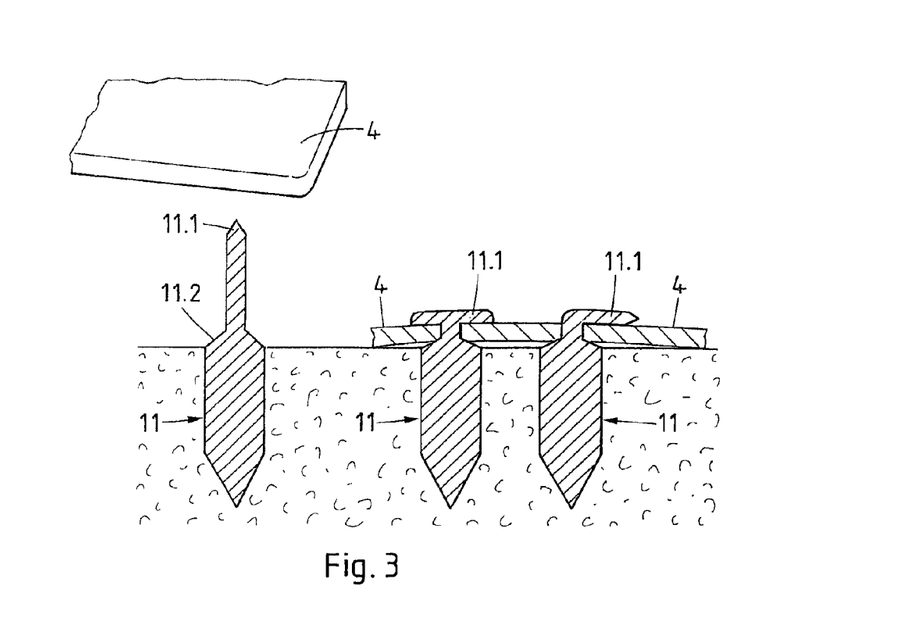
FIG. 3 shows an illustration of a further embodiment of an implant according to the invention.

FIG. 3 illustrates an embodiment of the invention where the implant 11 functions as a kind of rivet-like anchor for the fabric. The illustration on the left-hand side shows an implant inserted in bone tissue. In this and in all following figures the micro-interlocking of the liquefiable material with the bone tissue is not especially emphasized. The proximal side of the implant 11 comprises an element that may penetrate the fabric 4 when the implant is already inserted. In the shown embodiment, the element is a needle-like protrusion 11.1 capable of piercing the fabric when the fabric is placed on the bone tissue with the implant. The implant 11 further comprises a shoulder 11.2 to which ultrasonic vibrations may be applied when the implant is inserted in the bone tissue cavity. To this end, a sonotrode of a tool by which the implant is inserted has to be specifically shaped.

After the implant is inserted, as illustrated, for two alternatives, in the middle and on the right-hand side of FIG. 3, the element is deformed in a rivet-like manner so that the fabric may not be removed after deformation. For example, the protrusion 11.1 (or other element) may be deformed by ultrasonic vibrations impinging on it or possibly by simply applying a force on it with or without additional heating.

Therefore, in accordance with the embodiment of FIG. 3, the mechanical vibrations during implantation impinge on a first surface portion (being the shoulder in the illustrated embodiment) in order to couple the vibrations into the implant and to enable liquefiable material to melt and to interpenetrate structures of the bone material. Thereafter, after adding the flexible planar structure, a second surface portion of the implant is impinged with energy so as to deform the implant in the region of the second surface portion and to affix the flexible planar structure and the implant to each other. This energy may again be applied in the form of mechanical vibrations, or it may be applied in the form of heat, for example. The impinging of the second surface portion with energy may lead to an interpenetration of the implant and the flexible planar structure, for example, by having implant material melt and fill pores in the flexible planar structure if the flexible planar structure is a fabric.

The introduction of the implant and the deformation of the protrusion 11.1 may be combined in one step if the penetration of the fabric 4 by the protrusion is done before inserting the implant into the bone tissue. Also, this embodiment features the advantage that the strength of the anchoring in the bone tissue and of the attachment of the flexible planar structure to the bone tissue is height. Also, the rivet-like implant is relatively easy to insert.

Figure 4A:
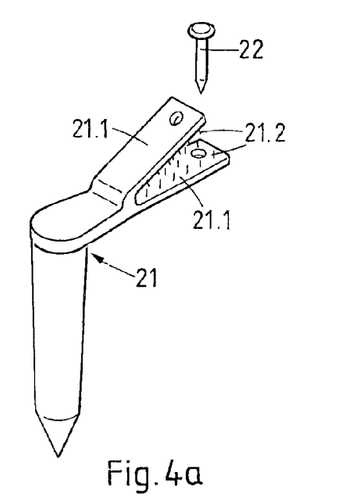
FIGS. 4a, 4b, 5a, 5b show embodiments of an implant with a plurality of micro-pins.
Figure 4B:
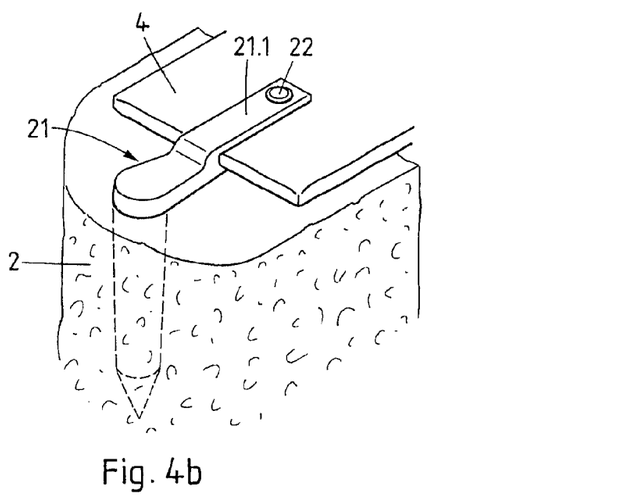
Figure 5A:
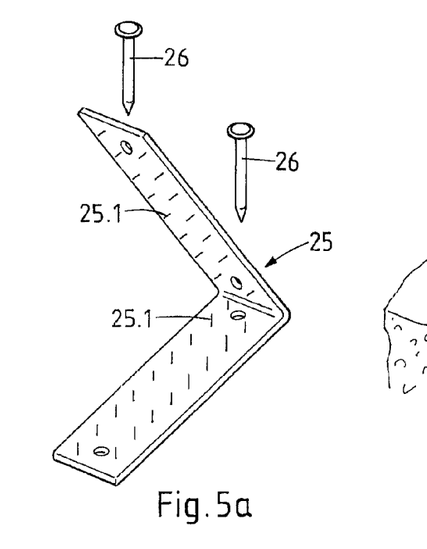
Figure 5B:
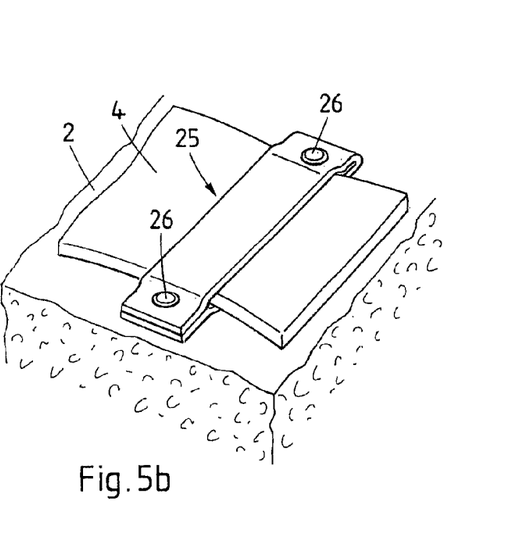

The embodiments illustrated in FIGS. 4a and 4b, and in FIGS. 5a and 5b, respectively, both rely on a common principle. A clamp element 21.1, 25 comprises two jaws which are swivellable relative to each other between an open state (illustrated in FIGS. 4a and 5a) and a closed state (illustrated in FIGS. 4b and 5b) of the clamp element. At least one of the jaws comprises a plurality of needle-like micro-pins 21.2, 25.1 capable of piercing the flexible planar structure when it is inserted between the jaws. The clamp element 21.1 shown in FIGS. 4a and 4b is a part of an implant 21 to be implanted in the above-described manner, whereas the clamp element 25 is separate from the at least one implant 26 by which it can be fastened to the bone tissue. The clamp elements may be fixed in their closed position by an additional implant 22, 26 as illustrated or by other means. Preferably, in any case, ultrasonic vibrations are used to close the clamp element.

The embodiment of FIGS. 4a through 5b feature the advantage that the fastening may relatively easily be revised.

Figure 6A:
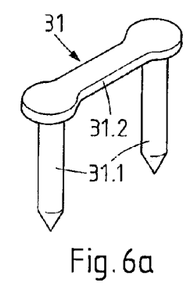
FIGS. 6a, 6b, 7a, 7b, 8a, 8b, illustrate embodiments of implants or multi-implant elements with bridge-like or claw-like structures.
Figure 6B:
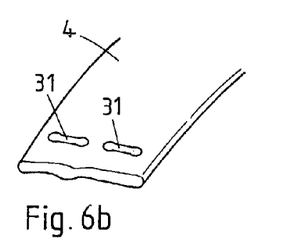
Figure 7A:
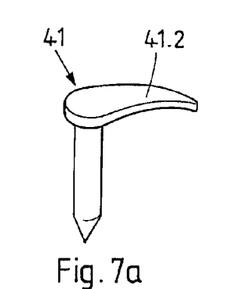
Figure 7B:
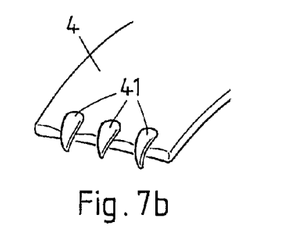
Figure 8A:
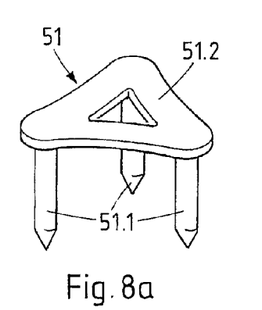
Figure 8B:
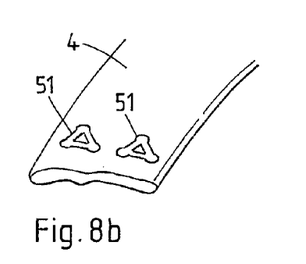

The implants in accordance with the embodiments of FIGS. 6a through 8b all include an area contact portion which is a portion that is essentially orthogonal to the implant axis. FIGS. 6a and 8a each illustrate a multi-implant element 31, 51, and FIG. 7a illustrates an implant 41. FIGS. 6b, 7b, and 8b show the multi-implant element 31, 51 or implant 41, respectively introduced into the bone tissue through the fabric 4 to be fastened thereto.

The multi-implant element 31, 51 of FIGS. 6a and 8a includes a plurality of implants 31.1, 51.1 which may comprise a tip-shaped distal end so that they can pierce the fabric 4 when being introduced in the bone cavity. They further include at least one bridge 31.2, 51.2 serving as the area contact portion. The area contact portion of the implant 41 of FIG. 7a is formed by a bent-off tapered bow (claw) 41.2 that is especially suited for being placed along an edge of the fabric 4. The bridge and the claw serve for stapling the fabric down and additionally may connect the implants. The multi-implant element or implant may be pre-fabricated to comprise the bridge or claw. As an alternative, for special applications the bridge or claw may also be added in situ.

An implant or multi-implant element according to any one of the above embodiments may, in addition, comprise further elements for carrying out further functions and not being shown in the above figures. Such further elements may include guidance and/or holding mechanisms for sutures (threads or wires) and/or straps etc., such as an eyelet etc.

Figure 9:
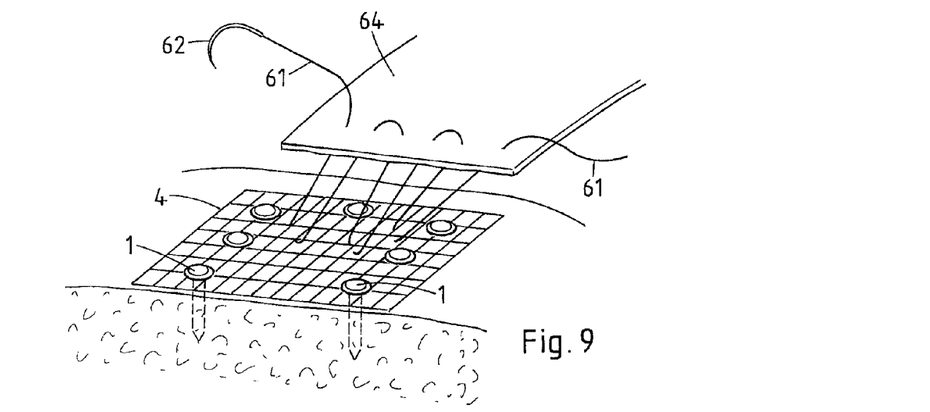
FIG. 9 shows a suturing base fastened by the method according to the invention.

The fabric 4 of FIG. 9 is fastened to the bone tissue in accordance with any embodiment of the invention, for example, any one of the embodiments previously described or illustrated in the following. In the illustrated version, the fabric 4 is attached by means of implants 1 of the kind illustrated in FIGS. 1 and 2. The fabric 4 serves as a pinned suturing fabric that may, for example, be used for suturing a ligament 64 or tendon to the bone. In this way it serves as universal base to suture down the ligament or tendon. The fabric 4 can further support the ligament or tendon integration by acting as scaffold and as a release system for growth factors. In the figure, a suture (thread or wire) 61 with a needle 62 is also shown.

For the embodiment of FIG. 9, the fabric may be especially coarsely meshed.

The embodiment features substantial advantages. Next to providing a strong and reliable connection between the bone and the ligament or tendon, the fabric is also easy to affix. It allows an excellent control of the tension of the ligament or tendon. The implantation brings about a low trauma only, especially if the implants are chosen to be comparably small. Both, the fabric relative to the bone tissue and the ligament or tendon relative to the fabric can be flexibly positioned, and the position of the ligament or tendon can easily be revised.

Referring to FIGS. 10 through 15, examples of applications of the invention are illustrated. In all figures, the implants and their connection to the flexible planar structure are illustrated only very schematically. It shall be understood that the above teaching referring to embodiments of the method, implant, and kit of parts applies to the illustrated applications and to further applications mentioned above.

Figure 10:
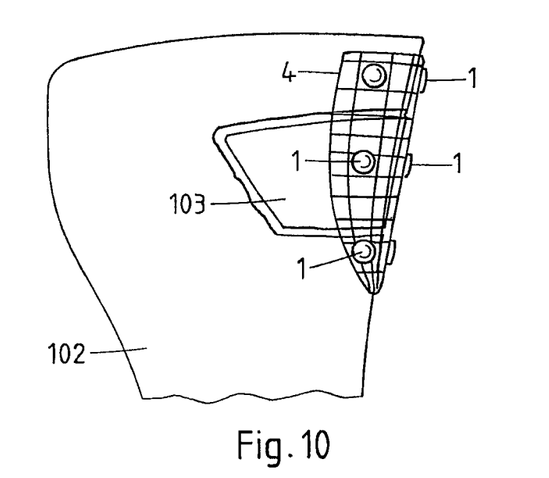
FIGS. 10-15 show applications of the method and device according to the invention.

FIG. 10 illustrates an application of the previously described method for fixing a flexible planar structure to bone tissue. A bone graft 103 is placed in a cavity formed by a recess in a bone tissue 102 (for example after a tumor operation) and is held in place in the cavity by means of a mesh 4. The mesh is attached to the bone tissue 102 and—optionally—also to the bone graft 103 by means of the method according to the invention.

Figure 11:
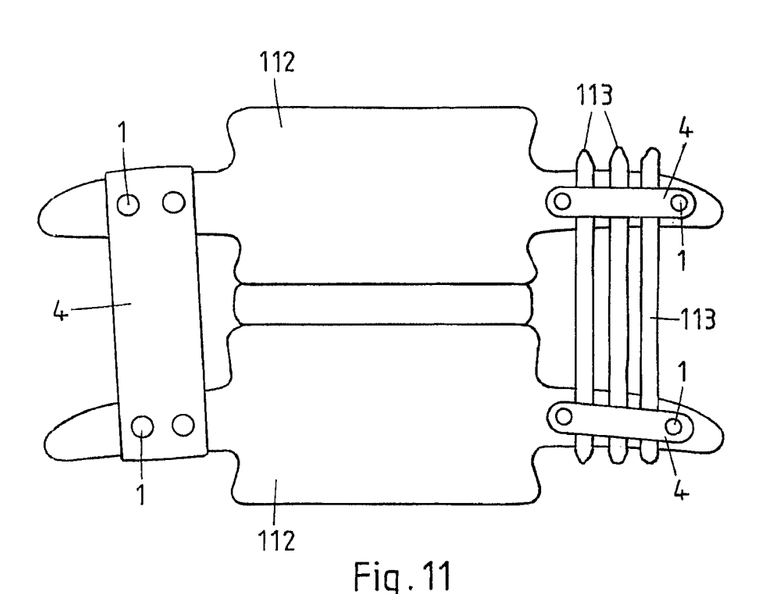

FIG. 11, illustrates yet another application of the previously described method for fixing a flexible planar structure to bone tissue. Two vertebrae 112 on the left-hand side are stabilized with respect to each other by means of a flexible planar structure 4 which is fixed to the two vertebrae by means of the method according to the invention. On the right-hand-side of the figure, the vertebrae are stabilized by means of bone fragments 113 which are fixed apically and caudally by a flexible planar structure 4. In the illustrated embodiment, the flexible planar structure is fastened to the vertebral bone tissue by implants 1 of the kind illustrated in FIG. 1.

Figure 12:
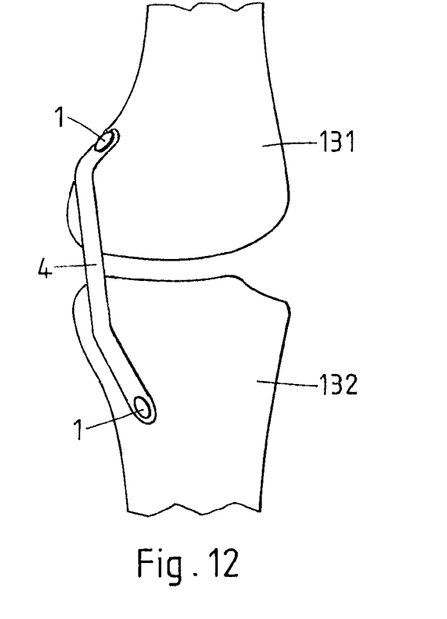

FIG. 12 shows a flexible planar structure serving as a ligament implant, namely as a substitute for the tibial collateral knee ligament connecting the femur 131 to the tibia 132.

Figure 13:
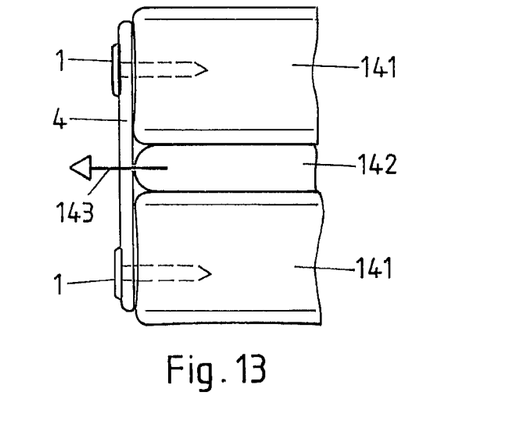

FIG. 13 concerns hernia repair and/or prevention. The flexible planar structure 4 in FIG. 13 is attached to two vertebral bodies 141 for preventing the (natural or artificial) intervertebral disc 142 between the vertebral bodies from sliding out in the direction of the arrow 143.

Figure 14:
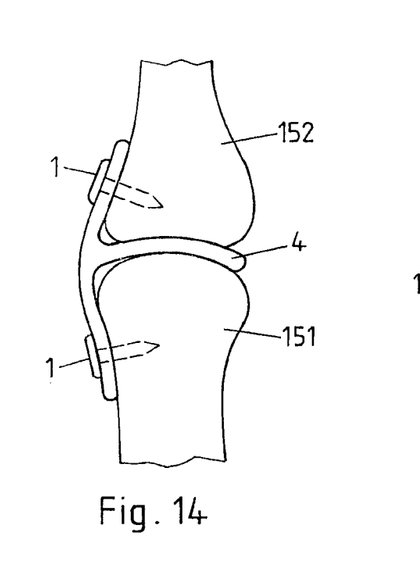

The flexible planar structure 4 of FIG. 14 serves as spacer between elements of an osteoarthritic joint. The figures very schematically shows portions of the metacarpal 151 and the proximal phalanx 152 of a human thumb, between which the flexible planar structure 4—being a fabric—acts as spacer.

Figure 15:
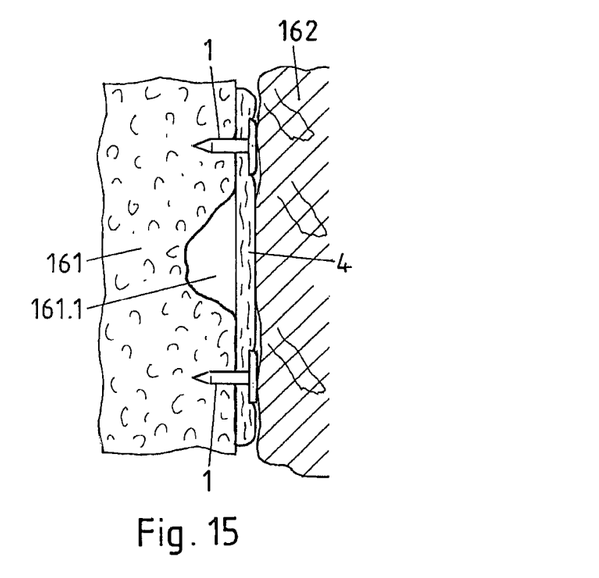

FIG. 15 shows a bone 161 with a cavity 161.1 that has been caused by bone harvesting. The flexible planar structure 4 serves for covering the cavity 161.1 during the re-growth process of the bone and for thereby preventing an organ 162 of soft tissue from being pressed into the cavity.

Figure 16:
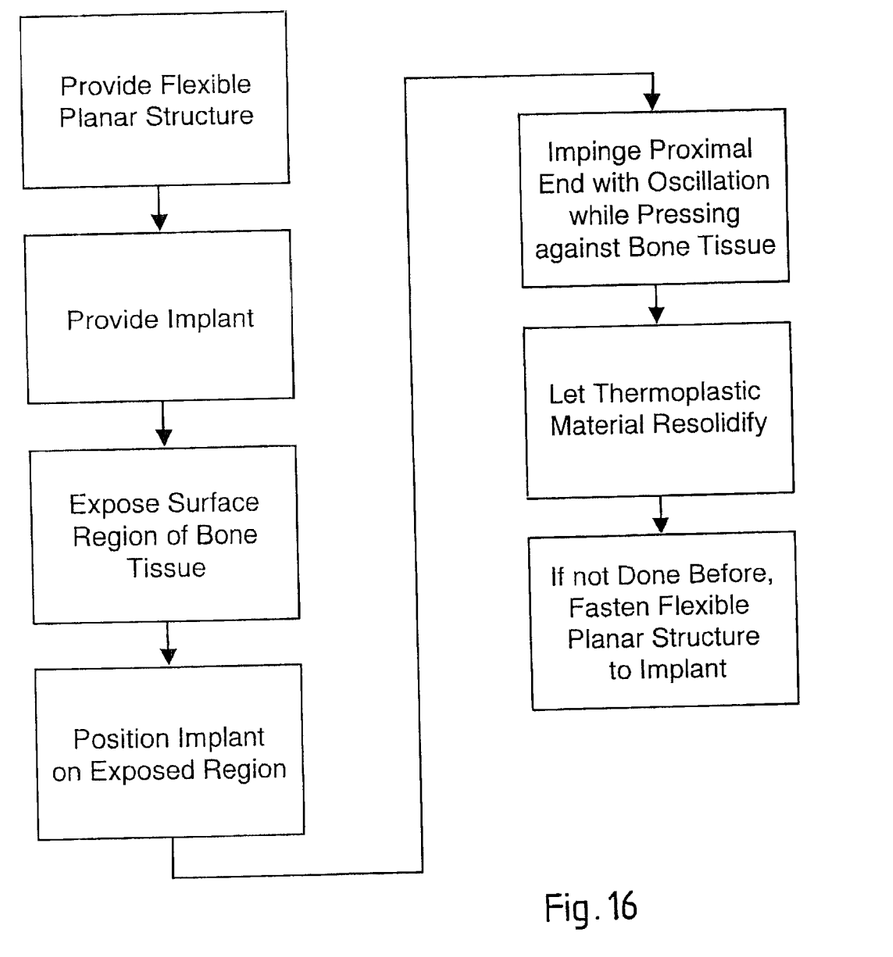
FIG. 16 shows a flowchart of the method according to the invention.

FIG. 16 shows a flowchart of an embodiment of the method according to the invention.

Figure 17:
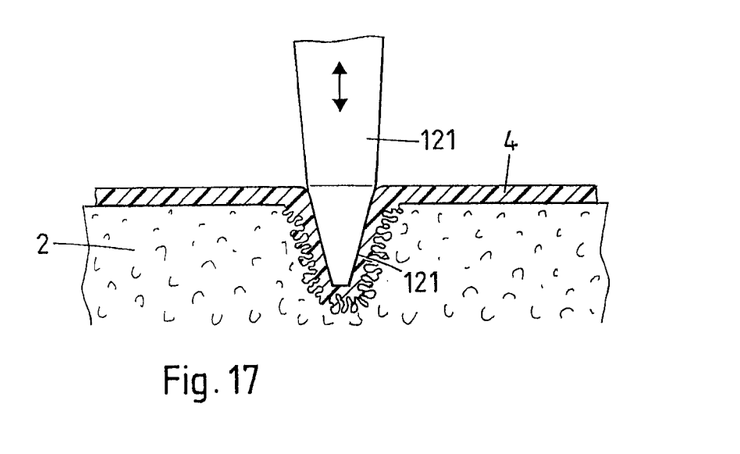
FIG. 17 discloses an embodiment where the implant is not pre-formed but formed in-situ.

FIG. 17, shows an embodiment of the invention where the implant is not pre-fabricated but formed in situ. To this end, a thermoplastic polymer film being the flexible planar structure 4 is placed on top of the bone tissue. Thereafter, a sonotrode is pushed through the polymer film and into the bone material while being subject to ultrasonic vibration. By this, a structure which protrudes into the bone tissue 2 is generated, said structure constituting the implant 121. The implant's 121 surface interpenetrates the porous bone tissue, by which effect the implant is anchored in the bone tissue.

Whereas in FIG. 17, a pin-shaped, needle-type sonotrode is shown, the sonotrode could equally well be a punch type sonotrode or have any other suitable shape.

Figure 18:
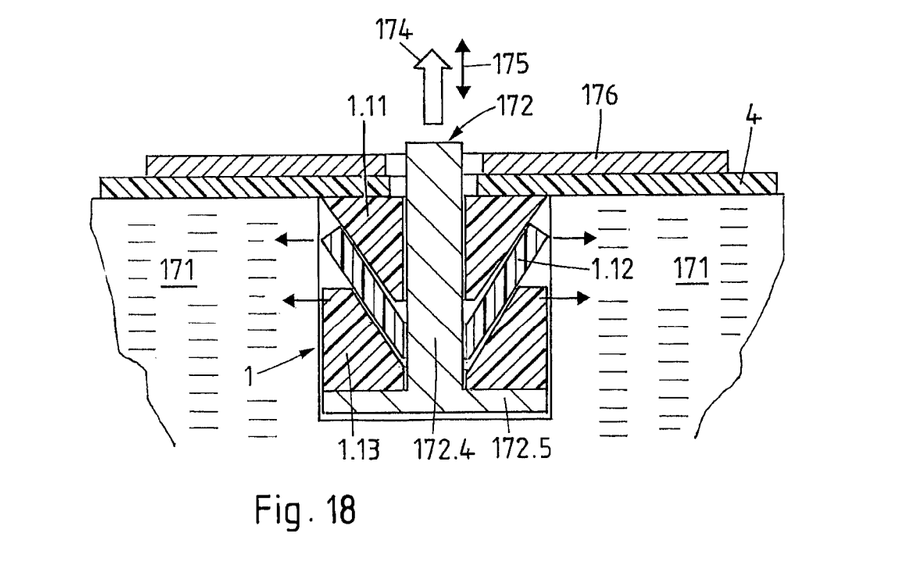
FIG. 18 discloses an embodiment where the connection between the implant and the flexible planar structure is achieved by applying a pulling force onto the implant.

FIG. 18, finally, illustrates an embodiment where the implant 1 and the flexible planar structure are intimately connected by means of a force pulling the implant towards the proximal side.

In the Figure, the implant is of a special construction including a plurality of components. 1.11, 1.12, 1.13. The components in the illustrated example are approximately symmetrical with regard to any rotation around its axis, which here serves as a compression axis. The first component 1.11 (seen from the distal side) has essentially the shape of a truncated cone, here with a continuous axial drilling (clearance). The second component 1.12 has essentially the shape of a hat, here with a central axial drilling. The third component 1.13 has here the shape of a cylinder with a conical clearance coaxial to the cylinder axis and a central drilling also coaxial to the cylinder axis. The central drillings of the first, second and third component are coaxial to each other and of approximately the same diameter. If applicable, deviating from the rotational symmetry, at least the central component 1.12, e.g. also the third component 1.13, possibly also the first component 1.11, are advantageously slit, which is not shown in the figure. Because of the slit(s) the relevant components are easily expandable and the implant as a whole can be compressed along the compression axis by a relatively moderate compression force. As the compression force 174 is introduced, the components 1.11, 1.12, 1.13 are moved along surfaces extending obliquely (i.e. at an angle, neither parallel nor perpendicular) to the compression force. This construction aims at causing peripheral surfaces of the components 1.11, 1.12, 1.13 to excerpt radial forces onto a wall of an opening in the hard tissue 171 when compressed along the compression axis. By this, the anchoring in of the implant in these circumferential walls instead of the distal base surface of the hard tissue opening is achieved. This effect is further described in the provisional U.S. patent application 60/826, 300, the teaching of which is incorporated herein by reference.

The vibrations and the force acting upon the implant are coupled into the implant by a tool 172, which is exposed to a pulling force. The tool 172 comprises a shaft 172.4 and a base plate 172.5. The shaft and/or the base plate can therein make up a substantial part of the cross-section of the whole configuration and form the load-bearing part, e.g. consisting of titanium, of the implant after implantation, i.e. after implantation, the tool does not have to be removable.

During the implantation procedure, a pulling force and mechanical vibrations are simultaneously coupled into the tool 172. This couples the mechanical vibrations and the pulling force—as compression force—into the implant. A counter pressure element 176 prevents the implant from being simply moved out of the opening. In the illustrated example, the counter pressure element 176 is designed as a plate.

The flexible planar structure 4 comprises an opening through which the shaft 172.4 protrudes. The diameter of the opening in the flexible planar structure is smaller than the diameter of the proximal thermoplastic implant surface, so that the flexible planar structure is in contact with the proximal thermoplastic implant surface. When the mechanical vibrations and the pulling force are applied between the tool and the counter element, the thermoplastic material of the implant melts in vicinity of the flexible planar structure. As a consequence:

if the flexible planar structure comprises pores, for example because of being a fabric, the thermoplastic material interpenetrates the pores and thereby, after re-solidifying, forms an intimate connection with the flexible planar structure.

if the flexible planar structure is thermoplastic and liquefiable under the conditions present during implantation, a weld connection is formed between the flexible planar structure and the implant.

If the flexible planar structure is neither porous nor thermoplastic—which is less preferred—, nevertheless a connection may be formed by the re-solidified thermoplastic material sticking to the surface of the flexible planar structure.

Following the implantation procedure the tool 172 can be applied in various ways:

The tool can remain in the place of the implantation. This embodiment is particularly advantageous when the tool is designed to simultaneously perform another function. Thus the tool can serve e.g. as an anchoring element for the attachment of a thread, a tape, a sinew, another bone, an endoprosthesis or any other element. It can also perform other functions known to be performable by implanted objects.

Providing the opening in the bone tissue is continuous, the tool can be separated from the vibratory device and removed from the distal side.

The tool can be removed from the proximal side. In this case the tool and the continuous opening in the implant, through which the shaft 172.4 is conducted during the implantation procedure, must be of a special shape not symmetrical at any angle with regard to the rotations, which is discussed in more detail below.

Embodiments of FIGS. 3, 4a/4b, 5a/5b, and 9 may also be implemented if the implant is not fixed by means of liquefying thermoplastic or otherwise liquefiable material, but is fixed conventionally or in another alternative manner, for example, as a screw or a conventional agraffe or the like. The embodiments of 6a/6b, 7a/7b, 8a/ab may also be implemented if the implant is not fixed by means of liquefying thermoplastic or otherwise liquefiable material, but is fixed conventionally or in another alternative manner and by means of retention structures such as shingles, riffles etc.

Whereas in the above-described embodiments, the flexible planar structure is placed on top of the bone tissue, this need not be the case. Rather, the flexible planar structure could, by means of an implant of appropriate length, be anchored in bone tissue through soft tissue like ligament, capsula, cartilage or other soft tissue. Thereafter, the flexible planar structure does not adhere to the bone tissue but to the soft tissue between the flexible planar structure and the bone tissue.

Various other embodiments may be envisaged without departing from the scope and spirit of the invention.

What is claimed is:

1. A surgical method comprising the steps of:
providing a structure, said structure being a textile, porous suturing fabric;
providing an implant, said implant comprising a proximal end, a distal end and a surface region, wherein
(A) there is solid material that is liquefiable by mechanical movement at the surface region of the implant, or
(B) the implant further comprises
(i) a hollow space that is at least partially filled by solid material that is liquefiable by mechanical movement, and
(ii) a plurality of channels between the hollow space and the surface region of the implant that allow liquefied material in the hollow space to reach the surface region of the implant when mechanical movement is applied to the solid material that is liquefiable by mechanical movement;
exposing a surface region of hard tissue or hard tissue substitute material;
positioning the structure relative to the exposed surface region of hard tissue or hard tissue substitute material;
manufacturing an opening in the structure positioned relative to the exposed surface region of hard tissue or hard tissue substitute material and causing the implant to reach through the opening and to contact the hard tissue or hard tissue substitute material;
fastening the implant to the hard tissue or hard tissue substitute material by:
impinging the proximal end of the implant with mechanical movement and simultaneously pressing the implant against the hard tissue or hard tissue substitute material while the distal end of the implant protrudes into the hard tissue or hard tissue substitute material such that at least a portion of the solid material becomes liquefied material and said liquefied material makes contact with the hard tissue or hard tissue substitute material and thereby causes at least a portion of the liquefied material to penetrate at least one of (i) unevenness, (ii) pores and (iii) artificially made retention structures of the hard tissue or hard tissue substitute material; and
letting the liquefied material resolidify to cause an interlocking of the implant and the hard tissue or hard tissue substitute material;
fastening the structure to the implant
before impinging the proximal end of the implant by mechanical movement,
while impinging the proximal end of the implant by mechanical movement, or
after impinging the proximal end of the implant by mechanical movement; and
suturing a flexible element to the suturing fabric after the implant has been fastened to the hard tissue or hard tissue substitute material.

2. The method of claim 1, wherein a plurality of implants is provided, each implant comprising a proximal end, a distal end and a surface region, wherein (A) there is solid material that is liquefiable by mechanical movement at the surface region of the implant, or
(B) the implant further comprises
(i) a hollow space that is at least partially filled by solid material that is liquefiable by mechanical movement, and
(ii) at least one channel between the hollow space and the surface that allow liquefied material in the hollow space to reach the surface region of the implant when mechanical movement is applied to the solid material that is liquefiable by mechanical movement,
wherein each one of said plurality of implants is fastened to the hard tissue or hard tissue substitute material, and
wherein the structure is fastened to each one of said plurality of implants
before impinging the proximal end of the implant by mechanical movement
while impinging the proximal end of the implant by mechanical movement, or
after impinging the proximal end of the implant by mechanical movement.

3. The method of claim 1, wherein fastening the structure to the implant includes liquefying, by mechanical movement, the solid material of the implant that is liquefiable by mechanical movement while the implant is in contact with the structure, and thereby forming a intimate connection between portions of the implant and of the structure.

4. The method of claim 3, wherein the step of fastening the structure to the implant includes causing the liquefied material of the implant to penetrate at least one of pores and of spaces of the structure and further includes letting the liquefied material to resolidify thereafter.

5. The method of claim 3, wherein the step of fastening the structure to the implant includes causing the liquefied material of the implant to weld to liquefied material of the structure.

6. The method of claim 1, wherein the structure is fastened to the implant ex situ before exposing the surface region of the hard tissue or hard tissue substitute material.

7. The method of claim 1, wherein fastening the structure to the implant includes letting the implant protrude through the opening manufactured in the structure.

8. The method of claim 7, wherein the implant further comprises a tip towering towards the proximal end, and wherein fastening the structure to the implant is done after impinging the implant by mechanical movement and comprises piercing the structure by the tip by applying the structure to the hard tissue or hard tissue substitute material and thereafter deforming the tip so as to affix the structure on the hard tissue or hard tissue substitute material.

9. The method of claim 8, wherein the tip is deformed by means of applying mechanical movement, and wherein material of the tip is liquefied by the mechanical movement and penetrates at least one of pores and of spaces of the structure.

10. The method of claim 7, wherein the implant is chosen to comprise a head-like or a claw-like structure and wherein after insertion of the implant said head-like or claw-like structure abuts to the structure.

11. The method of claim 1, wherein during the step of fastening the implant to the hard tissue, a force is applied to the implant in a direction towards the proximal end of the implant.

12. The method of claim 11, wherein by said force the implant is pressed against the structure.

13. The method of claim 1, wherein during the step of fastening the implant to the hard tissue, a force is applied to the structure in a direction toward the distal end of the implant, whereby the structure is pressed against the implant.

14. The method according to claim 1, wherein the step of manufacturing the opening comprises piercing the structure by the implant.

15. The method of claim 1, wherein the structure comprises pores, wherein either the solid material that is liquefiable by mechanical movement at the surface region of the implant is in contact with the structure during the step of impinging, or the implant further comprises a second surface region, and there is solid material that is liquefiable by mechanical movement at the second surface region of the implant that is in contact with the structure during the step of impinging, and wherein the step of impinging causes liquefied material to infiltrate the pores to form, after re-solidification, an anchoring of the implant also in the structure.

16. The method according to claim 1, wherein the flexible element is a ligament or a tendon.

17. The method according to claim 1, wherein the structure is provided with growth factors and acts as a release system for the growth factors.

\* \* \* \* \*